(12) United States Patent
Paczkowski et al.

(10) Patent No.: US 10,295,556 B1
(45) Date of Patent: May 21, 2019

(54) EVENT DETECTION USING PHYSICAL VIBRATION AND AUDIO SENSORS ON MOBILE DEVICES

(71) Applicant: Sprint Communications Company, L.P., Overland Park, KS (US)

(72) Inventors: Lyle W. Paczkowski, Mission Hills, KS (US); Jeffrey Ryan Miller, Overland Park, KS (US); Quinton Anthony Nicolace, Overland Park, KS (US); Brad Eugene Torrence, Eudora, KS (US); Nilofar Hadavandifard, Olathe, KS (US); Prabhakar Thennarasu, Edison, NJ (US)

(73) Assignee: Sprint Communications Company L.P., Overland Park, KS (US)

( * ) Notice: Subject to any disclaimer, the term of this patent is extended or adjusted under 35 U.S.C. 154(b) by 727 days.

(21) Appl. No.: 14/056,354

(22) Filed: Oct. 17, 2013

(51) Int. Cl.
  *G06F 11/00* (2006.01)
  *G01N 35/00* (2006.01)
  *A61B 5/08* (2006.01)

(52) U.S. Cl.
  CPC ........... *G01N 35/00* (2013.01); *A61B 5/0823* (2013.01)

(58) Field of Classification Search
  CPC ......... G01N 35/00; G01R 22/10; H04L 7/745
  USPC ..... 702/66, 71, 75, 122, 183, 188, 189, 193; 370/231; 705/26.3
  See application file for complete search history.

(56) References Cited

U.S. PATENT DOCUMENTS

| 8,964,543 | B1 * | 2/2015 | Roskind | H04L 47/365 370/231 |
| 2009/0287433 | A1 * | 11/2009 | Houston | G01R 22/10 702/62 |
| 2013/0346229 | A1 * | 12/2013 | Martin | G06Q 40/00 705/26.3 |

* cited by examiner

*Primary Examiner* — John H Le

(57) ABSTRACT

Methods and systems are provided for detecting the occurrence of events utilizing data taken from multiple mobile devices in a wireless communications network. At least a first set and a second set of data is received at the network from a first and second mobile device. The first and second sets of data corresponding to vibration and audio data taken from the mobile devices is analyzed to determine that each set of data corresponds to the occurrence of an instance of an event. An action to perform is then determined based on the occurrences of the instances of the event.

18 Claims, 8 Drawing Sheets

EVENT DETECTION USING PHYSICAL VIBRATION AND AUDIO SENSORS ON MOBILE DEVICES

SUMMARY

A high-level overview of various aspects of the invention are provided here for that reason, to provide an overview of the disclosure and to introduce a selection of concepts that are further described below in the detailed description. This summary is not intended to identify key features or essential features of the claimed subject matter, nor is it intended to be used as an aid in isolation to determine the scope of the claimed subject matter.

In brief and at a high level, this disclosure describes, among other things, a system where mobile devices act as individual sensors and are able to detect the occurrence of an instance of an event, such as a cough, sneeze, thunderstorm, lighting, explosion, earthquake, scream, crying, gunshots, etc. The data may be analyzed at the mobile device level or at the network level. Ultimately, a network component may determine that an event has occurred, and make predictions about the track of the event, such as the case of an earthquake, health-related illness, or thunderstorm, and may provide the data to one or more third party entities. Each of the mobile devices may have at least one of a vibrational sensor for detecting physical vibrations, and an acoustical sensor for detecting audio. When used together, many types of events may be quickly detected and monitored, if desired.

BRIEF DESCRIPTION OF THE SEVERAL VIEWS OF THE DRAWINGS

Illustrative embodiments of the present invention are described in detail below with reference to the attached drawing figures, and wherein.

DETAILED DESCRIPTION

Figure 1:
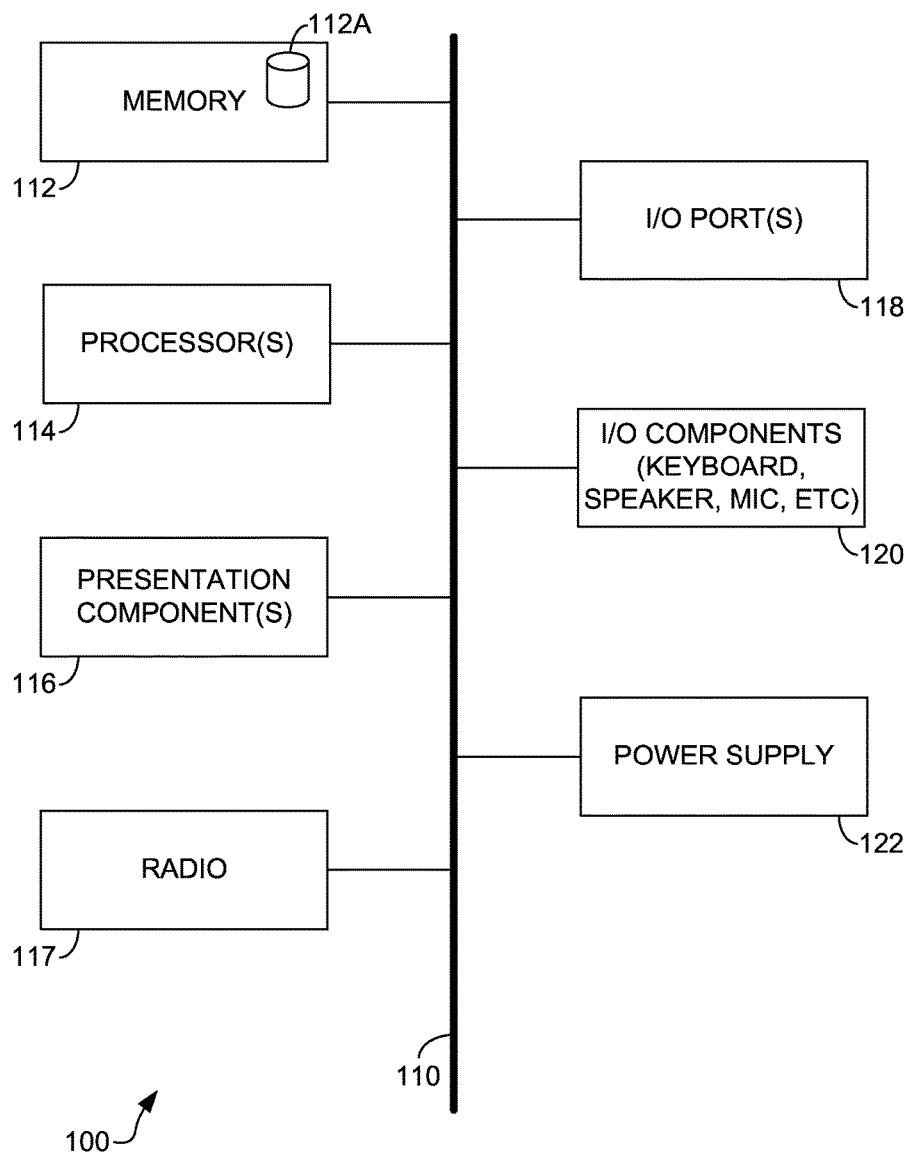
FIG. 1 depicts a block diagram of a mobile device in accordance with an embodiment of the present invention.

The subject matter of select embodiments of the present invention is described with specificity herein to meet statutory requirements. But the description itself is not intended to define what we regard as our invention, which is what the claims do. The claimed subject matter might be embodied in other ways to include different steps or combinations of steps similar to the ones described in this document, in conjunction with other present or future technologies. Terms should not be interpreted as implying any particular order among or between various steps herein disclosed unless and except when the order of individual steps is explicitly described.

Further, various technical terms are used throughout this description. A definition of such terms can be found in, for example, Newton's Telecom Dictionary by H. Newton, 27th Edition (2013). These definitions are intended to provide a clearer understanding of the ideas disclosed herein but are not intended to limit the scope of the present invention. The definitions and terms should be interpreted broadly and liberally to the extent allowed by the meaning of the words offered in the above-cited reference.

Embodiments of our technology may be embodied as, among other things, a method, system, or computer-program product. Accordingly, the embodiments may take the form of a hardware embodiment, or an embodiment combining software and hardware. In one embodiment, the present invention takes the form of a computer-program product that includes computer-useable instructions embodied on one or more computer-readable media.

Computer-readable media include both volatile and non-volatile media, removable and nonremovable media, and contemplate media readable by a database, a switch, and various other network devices. Network switches, routers, and related components are conventional in nature, as are means of communicating with the same. By way of example, and not limitation, computer-readable media comprise computer-storage media and communications media.

Computer-storage media, or machine-readable media, include media implemented in any method or technology for storing information. Examples of stored information include computer-useable instructions, data structures, program modules, and other data representations. Computer-storage media include, but are not limited to RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These memory components can store data momentarily, temporarily, or permanently.

Communications media typically store computer-useable instructions—including data structures and program modules—in a modulated data signal. The term "modulated data signal" refers to a propagated signal that has one or more of its characteristics set or changed to encode information in the signal. Communications media include any information-delivery media. By way of example but not limitation, communications media include wired media, such as a wired network or direct-wired connection, and wireless media such as acoustic, infrared, radio, microwave, spread-spectrum, and other wireless media technologies. Combinations of the above are included within the scope of computer-readable media.

As mentioned, embodiments of the present invention are directed toward the use of a plurality of mobile devices in different locations in a network to detect the occurrence of an event. Multiple mobile devices, in one instance, may detect various instances of an event in the form of data, and communicate this data to the network, which may use the data to determine if an event has occurred. An event, in one embodiment, is a health-related illness, such as the flu or a cold, but in other embodiments, may be an earthquake, a person (e.g., child) screaming for help, gunshots, a car door shutting, or any other event that can be detected by way of a mobile device. Mobile devices that are able to detect an instance of an event may have one or more sensors integrated therein, such as a vibrational sensor for detecting physical vibrations, and an audio sensor for detecting acoustical vibrations. In some embodiments, both a vibrational sensor and an audio sensor are integrated into a mobile device that is utilized to detect the occurrence of an instance of an event. Many mobile devices currently have both accelerometers and microphones, and thus would be able to detect physical and acoustical vibrations.

For example, in the case of a virus, infection, disease, or other health-related illness (e.g., cold and flu), the occurrence of physical manifestations of the health-related illness, such as coughing, sniffling, nose blowing, hoarseness, and sneezing, may be detected by mobile devices in network to allow for the network to detect the spread and movement of the health-related illness. These instances of an event (e.g., coughing, sniffling, nose blowing, hoarseness, sneezing) have unique and identifiable harmonic characteristics that can be detected and analyzed at the network level. In one embodiment, mobile devices in a building or a small region could be monitoring the beginning of a form of cough or sneeze by way of an algorithm and report frequencies and location pools. Over a larger region, the network could be fed similar information from a multitude of reporting appliances so that the network could analyze the direction of the virus movement. As the frequency and location shifts, medical groups could analyze and use this information for proactive patient care, such as to administer flu shots to elderly individuals who are located in a region where the illness is moving.

Alternatively, the devices having sensors thereon that are listening for the occurrence of an instance of an event may not be mobile devices, but instead may be some other type of a device that is statically positioned, as opposed to a mobile device whose location is dynamic. For instance, devices on train trusses may be able to detect issues with a train track based on physical vibrations and acoustical vibrations detected by vibrational and audio sensors on the devices. Similar devices may be utilized in regions where earthquakes are common, or in areas where gunshots may be heard. These events can be detected and used to alert the appropriate authorities. The use of both physical and acoustical vibration data allows the devices to provide data to the network so that the network is able to analyze and filter the data to determine an action to take, such as alerting authorities as to the occurrence of an event, providing health-related information to insurance companies or hospitals, etc.

In one embodiment, the mobile devices are able to communicate with one another and share data. In this embodiment, one of the mobile devices may be responsible for collecting data upon an occurrence of an instance of an event (e.g., a sneeze, a cough, an earthquake, a child screaming) that is detected by multiple devices and analyzing the data to filter the irrelevant data. For instance, if four mobile devices in a localized area (e.g., room, building) detect a single individual's sneeze, one of the mobile devices could collect the data and know to discard three of the instances of the sneeze, as there was only one sneeze, not four. In alternative embodiments, the network has the capability to collect all of the data and determine what to keep and what to discard. In still other embodiments, the mobile devices could each filter out irrelevant data and send just the relevant data corresponding to the occurrence of the instance of the event to the network.

In embodiments, either a mobile device or the network determines that an instance of a particular event has occurred. In one embodiment, this is determined by use of semaphores, which entails the conversion of audio and vibrational data into a representative form of basic shapes. These shapes take very little information, and are easy to store. The transmission of data regarding the representative shape to the network is fairly quick. As used herein, a semaphore is a variable or abstract data type that provides a simple but useful abstraction for a vibration analog that is collected at a device, such as a machine-to-machine sensor or a mobile device. As such, digital or analog data that represents data from the sensors on a device may be converted into an electronic shape, or a digital semaphore, such that the network or device can determine the instance of an event that has occurred.

In a first aspect of the present invention, a method is provided for detecting an occurrence of an event based on data taken by a plurality of mobile devices. The method includes receiving a first set of data from a first mobile device, receiving a second set of data from a second mobile device, and analyzing the first and the second sets of data. Each of the first and the second sets of data corresponds to vibration and audio data taken from the first and the second mobile devices. The method further includes determining that each of the first and the second sets of data corresponds to the occurrence of an instance of an event, and based at least on the occurrences of the instances of the event, determining an action to perform.

In a second aspect of the present invention, computer-readable media having computer-executable instructions embodied thereon are provided that, when executed, perform a method for detecting an occurrence of an event based on data taken by a plurality of mobile devices. The method includes, at a first mobile device, determining that a first set of data received by a vibrational sensor and an audio sensor on the first mobile device corresponds to a first instance of an event. The method also includes receiving a second set of data from a second mobile device, the second set of data corresponding to a second instance of the event. The first and the second mobile devices communicate with one another by way of a wireless communications network. Further, the method includes determining, by the first mobile device, that the second set of data corresponds to a second instance of the event, and determining, by the first mobile device, whether the second instance is duplicative of the first instance of the event. If the second instance is duplicative of the first instance, discarding the second set of data that corresponds to the second instance of the event, and if the second instance is not duplicative of the first instance, retaining both the first set of data and the second set of data. Also, the method includes communicating data associated with one or more of the first instance and the second instance of the event to a network component in the wireless communications network, the network component analyzing the data associated with the one or more of the first instance and the second instance and the data received from a plurality of other mobile devices to determine an action to be performed based on the occurrence of the event.

In a third aspect of the present invention, a method is provided for detecting an occurrence of an event based on data taken by a plurality of mobile devices. The method includes, at a first mobile device, receiving data from a vibrational sensor and an acoustical sensor integrated with the first mobile device, the data representing the occurrence of a first instance of an event. The method also includes generating a representation of the data illustrating a waveform of frequency of one or more of sound or vibration over time, and based on the waveform, identifying at least one shape of the waveform, the at least one shape of the waveform containing at least a majority of the waveform therein. Further, the method includes identifying the event based on the at least one shape of the waveform, and communicating a portion of the data associated with the at least one shape of the waveform to a network component in the wireless communications network. The network component receives from a plurality of mobile devices a plurality of data representing the occurrences of other instances of the event, and the network component analyzes the portion of the data and the plurality of data to determine an action to be performed based on the occurrences of the first instance and the other instances of the event.

Turning now to FIG. 1, a block diagram of an illustrative mobile device is provided and referenced generally by the numeral 100. Although some components are shown in the singular, they may be plural. For example, mobile device 100 might include multiple processors or multiple radios, etc. As illustratively shown, mobile device 100 includes a bus 110 that directly or indirectly couples various components together including memory 112, a processor 114, a presentation component 116, a radio 117, input/output ports 118, input/output components 120, and a power supply 122.

Memory 112 might take the form of one or more of the aforementioned media. Thus, we will not elaborate more here, only to say that memory component 112 can include any type of medium that is capable of storing information in a manner readable by a computing device. Component 112A may be an application or code that is stored on device 100 that carries out one or more processes, as described herein. Processor 114 might actually be multiple processors that receive instructions and process them accordingly. A processor used in embodiments described herein would be programmed to listen for specific sounds or other vibrations. Presentation component 116 includes the likes of a display, a speaker, as well as other components that can present information (such as a lamp (LED), or even lighted keyboards).

Radio 117 represents a radio that facilitates communication with a wireless telecommunications network. Illustrative wireless telecommunications technologies include CDMA, GPRS, TDMA, GSM, LTE, LTE Advanced, HRPD, eHRPD, EVDO, and the like. In some embodiments, radio 117 might also facilitate other types of wireless communications including Wi-Fi communications and GIS communications.

Input/output port 118 might take on a variety of forms. Illustrative input/output ports include a USB jack, stereo jack, infrared port, proprietary communications ports, and the like. Input/output components 120 include items such as keyboards, microphones, touchscreens, and any other item usable to directly or indirectly input data into mobile device 100. In embodiments of the present invention, input/output components 120 include acoustical and vibrational sensors, such as a microphone and an accelerometer. Other types of sensors may be utilized that are able to detect physical and acoustical vibrations. Power supply 122 includes items such as batteries, fuel cells, or any other component that can act as a power source to power mobile device 100. As mentioned above, a processor that is able to listen for specific sounds and physical vibrations is used in embodiments described herein. This processor would conserve power consumption of the mobile device's battery, as the mobile device could potentially be in a listening state at all times.

Figure 2:
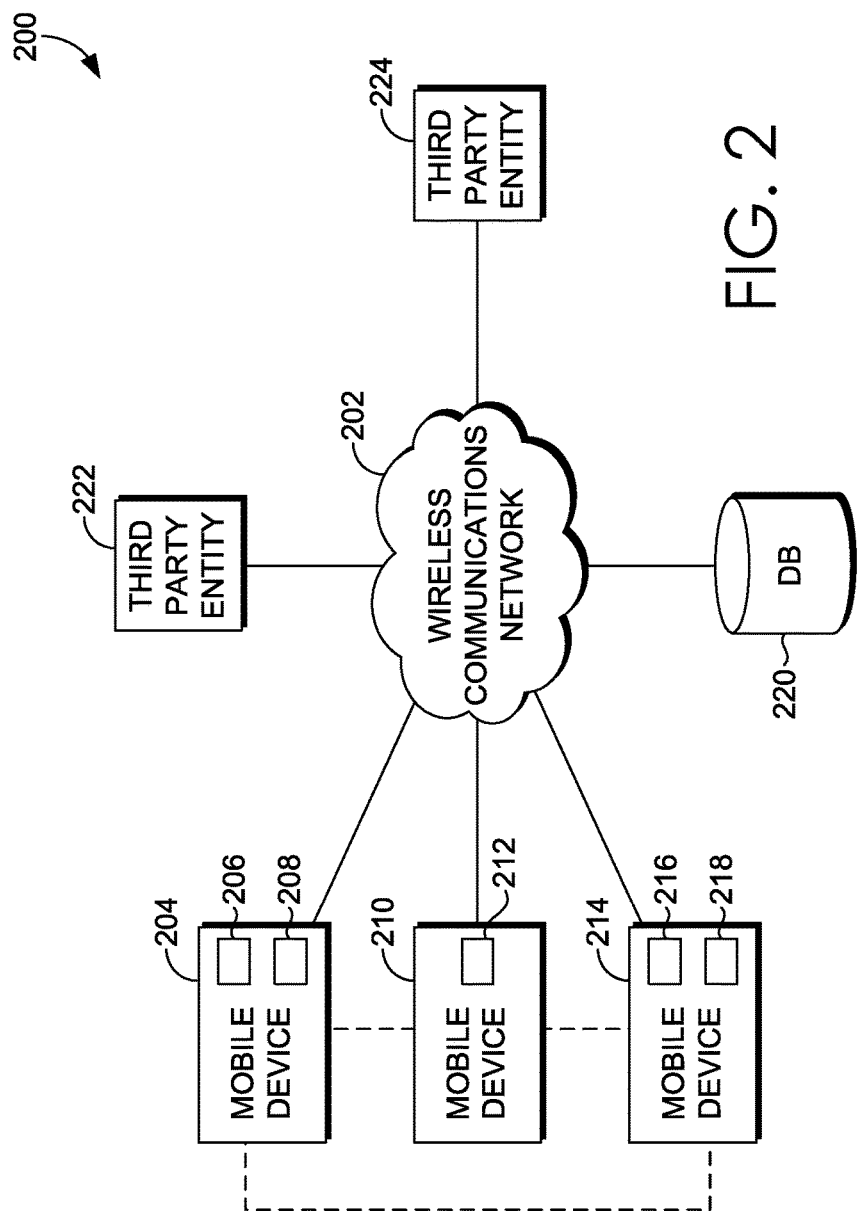
FIG. 2 depicts an illustrative operating system for carrying out embodiments of the present invention.

FIG. 2 depicts an illustrative operating environment, referenced generally by the numeral 200, and illustrates an illustrative networking environment that enables multiple devices to communicate with one another, and/or to communicate with a network. The illustrative operating environment 200 shown in FIG. 2 is merely an example of one suitable operating environment and is not intended to suggest any limitation as to the scope of use or functionality of embodiments of the present invention. For example, while three mobile devices are illustrated in FIG. 2, many more devices may actually be utilized in the detection of an event, such as at least hundreds, or at least thousands, or at least hundreds of thousands, or at least one million devices may be used. Additionally, other networks not illustrated in FIG. 2 are contemplated to be within the scope of the present invention.

Mobile devices 204, 210, and 214, in one embodiment, are the type of device described in connection with FIG. 1 herein. The mobile devices 204, 210, and 214 may support one or more technologies, such as CDMA 1×A, GPRS, EvDO, TDMA, GSM, WiMax technology, LTE, LTE Advanced, eHRPD, and the like. Any and all such aspects, and any combination thereof, are contemplated as being within the scope of the invention. The mobile devices 204, 210, and 214 may include a client application that helps carry out aspects of the technology described herein. The client applications may each be a resident application on the handset used by the mobile device to carry out various aspects of embodiments of the present invention. More specifically, the client applications may allow the mobile devices 204, 210, and 214 to form a small or local network with one another to communicate data with each other. The communication of data allows one of the devices to determine whether an instance of an event has occurred, and to filter any data that is irrelevant, such as repeated data (e.g., multiple sets of data representing the same occurrence of an instance of an event). Reference to an application, software, or the like, is referring to one or more computer-readable media that are embodied with a set of computer-executable instructions that facilitate various actions to be performed. We will not always include this lengthy terminology because doing so would make this document more difficult to read.

Each of mobile devices 204, 210, and 214 may include one or more sensors that receive vibrational data, such as audio data, such as from a microphone, or physical vibrational data, such as from an accelerometer. For instance, mobile device 204 includes a vibrational sensor 206 and an audio sensor 208. Mobile device 210 includes one sensor 212, which may be either audio or vibrational. Mobile device 214 includes both a vibrational sensor 216 and an audio sensor 218. Each sensor is capable of listening for and detecting particular sounds or physical vibrations. Also contemplated to be within the scope of the present invention are sensors that are capable of detecting temperature and movement.

FIG. 2 additionally depicts a wireless communications network 202, also termed a core network. A wireless communications network may comprise one or more components not illustrated in FIG. 2, including one or more cell towers, access components or base stations, RNCs, gateways, etc. Not all connections or possible connections are shown. An access component, not shown, may be one or more of a base transceiver station (BTS) tower, eNodeB, a Wi-Fi Router, a Mobile Hotspot, and any other device that facilitates communication between the mobile devices 204, 210, and 214 and the network 202. For example, if the wireless communications system utilizes LTE technology, the access component would be termed eNodeB. In one embodiment, the access component includes both a Wi-Fi Router and a BTS tower. In another embodiment, access component is a BTS tower.

A radio network controller (RNC), not shown, performs various functions, such as managing radio channels, power control, load control, admission control, packet scheduling, handover control, macrodiversity, security functions, and mobility management. A base station controller (BSC) (not shown) acts as the intelligence behind base transceiver stations (BTS) and handles allocation of radio channels, receives measurements from mobile devices, and controls handovers from one BTS to another BTS. The hardware associated with the access components may include, for example, the actual radio mast or tower, as well as antennas, transceivers, GPS receivers, electrical power sources, digital signal processors, control electronics, and the like that are associated with the radio tower.

Wireless-telecommunications links between each of the mobile devices 204, 210, and 214 and an access component may be a short-range connection, a long-range connection, or a combination of both a short-range and a long-range wireless telecommunications connection. When we refer to "short" and "long" types of connections, we do not mean to refer to the spatial relation between two devices. Instead, we are generally referring to short-range and long-range as different categories, or types, of connections (i.e., a primary connection and a secondary connection). A short-range connection may include a Wi-Fi connection to a device (e.g., mobile hotspot) that provides access to a communications network, such as a WLAN connection using 802.11 protocol. A short-range connection may also utilize mobile broadband, which provides wireless Internet access using a mobile broadband router. One example of mobile broadband technology is Evolution Data Optimized, or EVDO. EVDO relies on a signal from a wireless tower rather than a physical connection like a phone line or cable. An EVDO modem receives the signal and allows a user to connect to the Internet. Another example of mobile broadband is HSPA. A long-range connection may include a connection using one or more of CDMA, GPRS, GSM, TDMA, and 802.16.

Embodiments of the present invention may be used with different technologies or standards, such as, for example, CDMA, 1xA, EVDO, HRPD, eHRPD, LTE, and LTE Advanced. Other technologies and standards not listed herein are also contemplated to be within the scope of the present invention.

In one exemplary embodiment, mobile devices 204, 210, and 214 are co-located, such as in the same area, region, room, building, etc. In this embodiment, when one person in the area coughs, each of the mobile devices 204, 210, and 214 may detect that a sneeze has occurred. This sneeze is referred to herein as an instance of an event. The event may be a health-related illness, such as a cold or flu. In the case that all three mobile devices 204, 210, and 214 detect the same cough, either one of the mobile devices, the network, or both has the capability to determine that there was just one cough. Therefore, the data from only one of the devices, such as the mobile device associated with the individual who coughed, is kept, and the data from the other mobile devices is discarded. The mobile device or the network would have the intelligence to analyze the data, based on the location of the mobile devices and the time stamp associated with the data, and determine which data to retain and which to discard.

Once the wireless communications network 202 receives the data from the mobile devices 204, 210, 214, and likely many others, the network 202 is able to determine whether an event has occurred, and if so, what the event is. For example, the network 202 may determine from the data that based on the quantity of coughs having occurred in a specific region over a certain amount of time that the event is a cold, is spreading in the region from where the data is received, and is moving in a certain direction. For instance, the network may notice that the number of coughs in Wichita, Kans. has significantly grown over the past 48 hours, and based on location data, the coughs are moving toward Kansas City, Kans. This data may be aggregated and communicated to a third party entity 222 and/or 224, which may be medical insurance companies, hospitals, governmental organizations, etc. These third party entities 224 and 224, in one embodiment, may pay to receive this data. Governmental organizations, such as the Center for Disease Control, may also be the recipient of this type of healthcare-related data, and would be able to use the precise location and time information to inform residents in regions where a particular illness is moving. The data may be stored by the network in a database 220, and may be retrievable at a later time.

Figure 3:
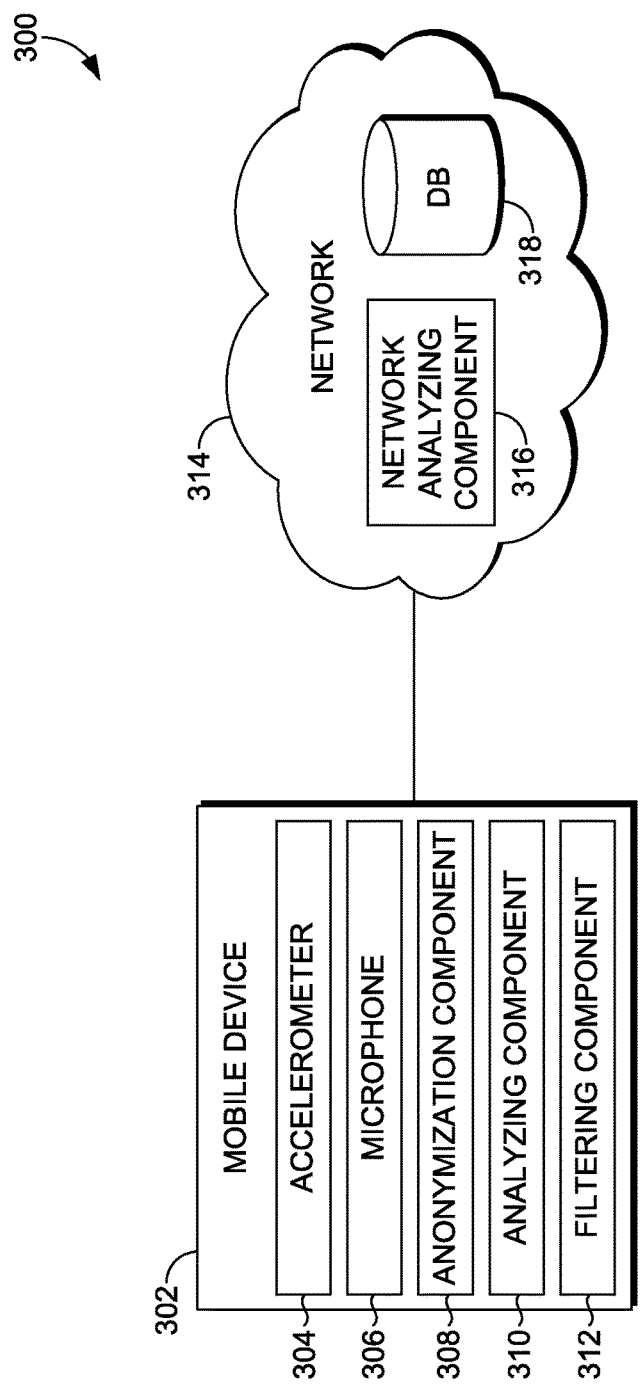
FIG. 3 depicts an illustrative mobile device in communication with a network, in accordance with an embodiment of the present invention.

FIG. 3 depicts an illustrative mobile device in communication with a network, depicted generally as numeral 300, in accordance with an embodiment of the present invention. The mobile device 302 includes an accelerometer 304, a microphone 306, an anonymization component 308, an analyzing component 310, and a filtering component 312. The accelerometer 304 is a device that may be incorporated into the mobile device 302, and that may be used to sense orientation, coordinate acceleration, vibration, shock, etc. In one embodiment, the accelerometer 304 is used to measure motion and vibration of a structure that is exposed to dynamic loads, which may originate from a human or other living being walking/running, earthquakes, aftershocks, vehicle collisions, wind gusts, explosions, etc. Each of these may be considered to be an event that can be detected, at least in part, by the accelerometer 304. The microphone 306 is an acoustic-to-electric transducer or sensor that converts sound into an electrical signal. The microphone 306 may use electromagnetic induction, capacitance change, piezoelectric generation, or light modulation to produce an electric voltage signal from mechanical vibration.

The anonymization component 308 strips the data of any identifying information, such as any data that may identify the user or the mobile device. Location data may be kept, but in embodiments, may be genericized so that the precise location of the mobile device at the time the data is taken is unknown. Embodiments of the present invention do not require personal information about users of the mobile devices that detect the events, but instead seek to determine when an event has occurred, and in some cases, the path of the event, such as the case of a health-related illness, a thunderstorm, an earthquake, etc. As such, a location is used to know where the various instances of an event have occurred. In these cases, personal identifiable information is not communicated through the network, but instead is scrubbed before leaving the mobile device 302. In an alternative embodiment, the mobile device 302 may send raw data to the network, and a network component may anonymize the data so that real user information is not transmitted outside of the network, nor can it be calculated or otherwise determined.

The analyzing component 310 analyzes data taken from the accelerometer 304 and/or the microphone 306. In one embodiment, two or more mobile devices are in communication with one another such that one of the mobile devices collects data regarding multiple instances of an event detected by the two or more mobile devices and determines what the event is, and may even filter the data so as to communicate only the relevant data to the network. As mentioned, the mobile device 302, by way of the analyzing component 310, may utilize shapes to determine the type of event that has occurred. For example, data may be converted into a graph depicting frequency over time. The graph, depending on the event, may take the form of a shape. This will be discussed in more detail herein with respect to FIGS. 4 and 5. The filtering component 312 is responsible for discarding irrelevant data prior to sending the data to the network 314. This may be done after the analyzing component 310 identifies a shape that best corresponds to the graphical representation of the data. The data not included within the shape may be discarded and not communicated to the network 314.

The network 314 includes, at least, a network analyzing component 316 and a database 318. The network analyzing component 316 is responsible for collecting and analyzing data received from the mobile device 302 and other mobile devices in the network. For instance, upon the mobile device 302 detecting, by way of one or more sensors, that an instance of an event has occurred (e.g., earthquake, sneeze, cough, scream, gunshots), the mobile device 302 may, in one embodiment, analyze the data and send filtered and relevant data to the network analyzing component 316 for further analysis. In another embodiment, the mobile device 302, upon detecting the occurrence of an instance of an event, may send the raw data to the network such that the network analyzing component 316 receives raw data from many mobile devices and is responsible for determining if an instance of an event has occurred, and to which event the instance corresponds. In both cases, the network analyzing component 316 is responsible for aggregating the data and storing it in the database 318. The data may then be retrieved and provided to a third party entity, as previously described.

Figure 4:
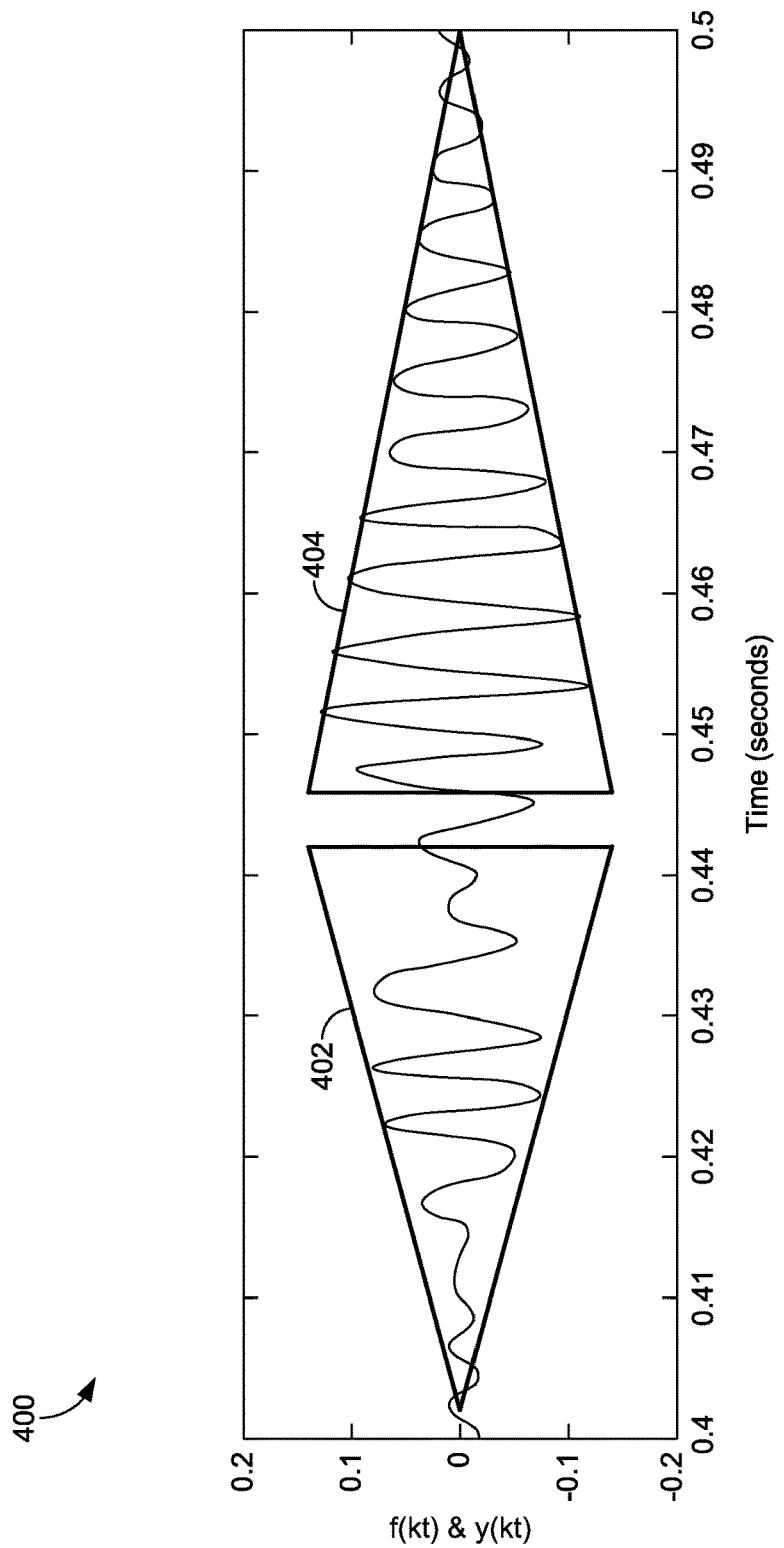
FIG. 4 depicts a waveform of frequency over time having identified shapes, in accordance with an embodiment of the present invention.

Turning now to FIG. 4, a waveform is shown representing frequency over time having identified shapes, in accordance with an embodiment of the present invention. The waveform graph of FIG. 4 is generally referred to by numeral 400. FIG. 4 illustrates how analog or digital data can be simplified into a shape, such as a digital semaphore, thus translating the data into actionable information that can be analyzed and distributed to solve a problem, or to inform a group, such as a third party entity. The embodiment of FIG. 4 represents a short cough, and is provided as merely an example. Other instances of an event may be represented by different shapes or forms and of different quantities of shapes, such as one or more shapes for a particular instance of an event.

In the case of FIG. 4, a short cough may be represented by two triangles 402 and 404. Either the mobile device that detects the short cough or the network may have the capability to correlate the frequency over time of a short cough with the two triangle shapes. While no two short coughs will look exactly the same when represented in a graph format such as the waveform graph 400, they are similar enough such that the two triangles 402 and 404 will generally correspond to most short coughs. In one instance, the one or more shapes that correspond to an instance of an event are predetermined and are saved either on the network or on individual mobile devices, depending on which is responsible for identifying the event that has occurred. For instance, when a person coughs, the mobile device and/or the network may already know that the shapes shown in FIG. 4 correspond to a short cough. As such, the shapes vary by event, not by person. If the same shapes (e.g., two triangles) fit the waveform graph of the person's cough, it can be determined that a cough has occurred, and can be correlated to other coughs that have been detected. In some embodiments, the data communicated to the network includes a time stamp and location information. The time stamp indicates a precise time at which the instance of the event was detected by a mobile device. Not only does this allow the network to know when the instance occurred and to generate the waveform graph of frequency over time, but also to discard duplicate instances of an event detected by more than one device.

Figure 5:
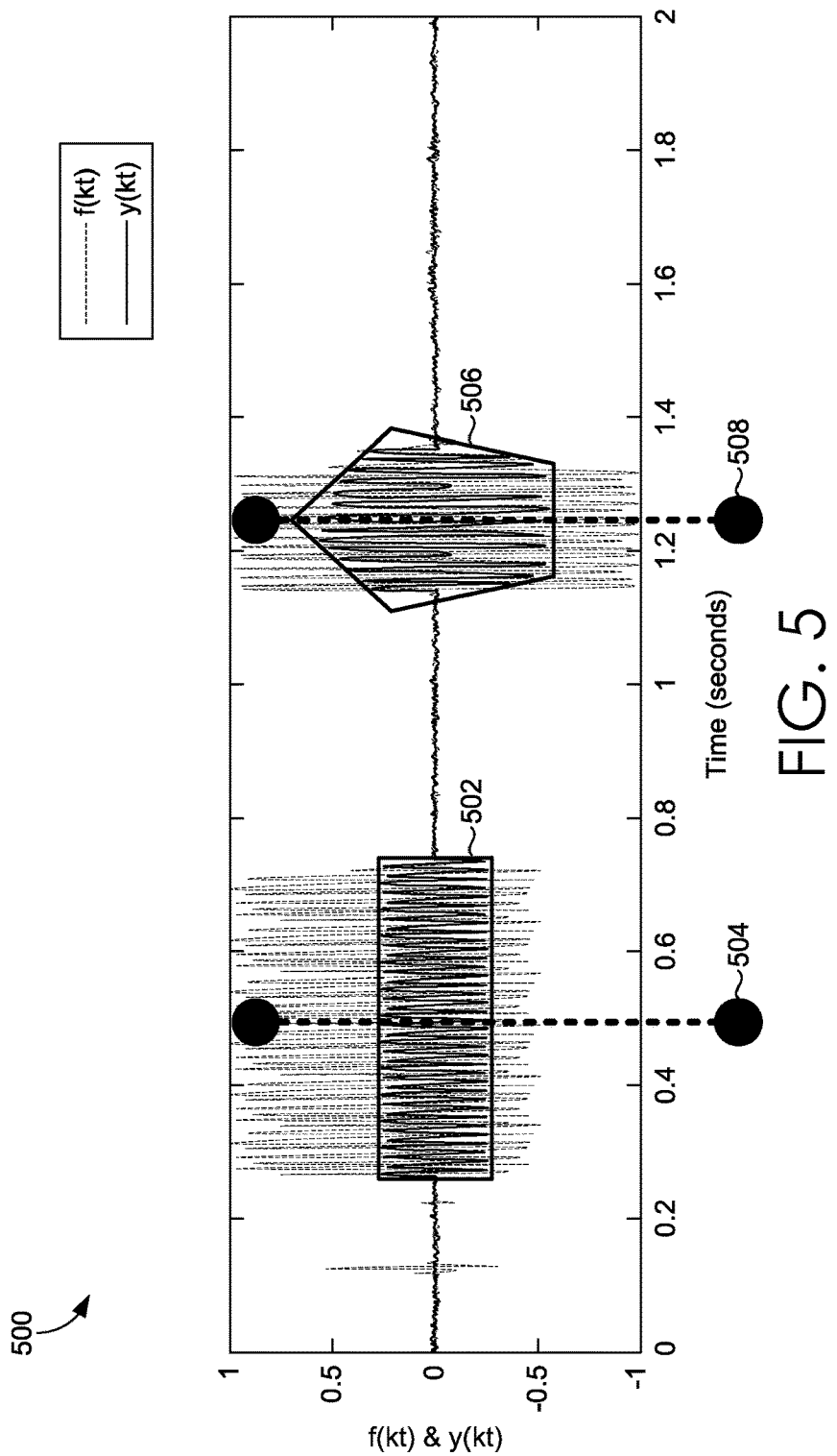
FIG. 5 depicts another waveform of frequency over time having identified shapes, in accordance with an embodiment of the present invention.

FIG. 5 depicts another waveform of frequency over time having identified shapes, in accordance with an embodiment of the present invention, and referred to generally as numeral 500. Here, a first shape 502 corresponds to a time stamp 504, while a second shape 506 corresponds to a time stamp 508. In the embodiment of FIG. 5, shape 502 may correspond to an instance of an event on its own, or in embodiments and is combined with shape 506 to represent an instance of a different event. There are many combinations of shapes that can be predetermined and used to identify an instance of an event that has occurred. The shape is determined based on the general shape of the waveform. In some embodiments, the shape is identified based on a certain percentage of the waveform fitting into the boundaries of the shape. For example, in one embodiment, at least 50% of the waveform is encompassed into the boundaries of the shape for the shape to correspond to that particular waveform. In other embodiments, at least 60%, at least 70%, at least 80%, or at least 90% of the waveform is encompassed into the boundaries of the shape for the shape to correspond to that particular waveform. A higher percentage would encompass more variations of a particular instance of an event, such as more coughs or sneezes, than would be detected if a lower percentage were used, although a lower percentage provides for higher accuracy.

As mentioned, allowing the mobile device to analyze the raw data and transform it into a known shape allows the mobile device to communicate an instance of an event instead of raw data to the network. The mobile device may instead communicate the shape (e.g., lengths of lines, angles), a timestamp associated with the instance of the event, magnitude information (e.g., how loud the instance of the event was), and other data that would allow the network to use the received data to determine whether the instance is part of a known event, or whether an event may be forming (e.g., cold, flu, thunderstorm).

Figure 6:
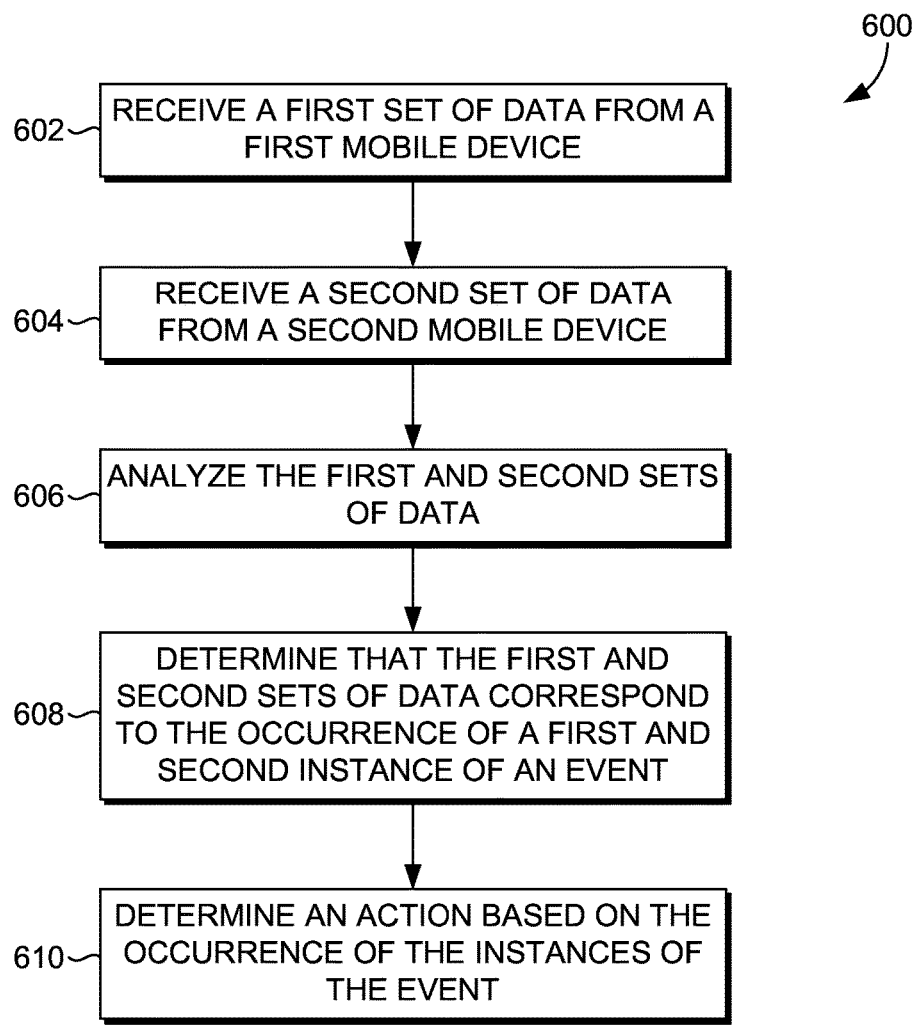
FIGS. 6-8 depict flow diagrams of methods for detecting an occurrence of an event based on data taken by a plurality of mobile devices, in accordance with embodiments of the present invention.

Referring to FIG. 6, a flow diagram is illustrated of a method 600 for detecting an occurrence of an event based on data taken by a plurality of mobile devices, in accordance with an embodiment of the present invention. Initially, at step 602, a first set of data is received from a first mobile device. A second set of data is received from a second mobile device at step 604. In embodiments, the first and second sets of data are received at a network component in a wireless communications network that receives and analyzes the received data. The first and second sets of data may comprise a time stamp associated with the occurrence of the instance of the event, frequency over time data, and location data. In one embodiment, the data is anonymized by each mobile device prior to being communicated to the network. At step 606, the first and second sets of data are analyzed. The data corresponds to vibration and audio data taken from sensors (e.g., vibrational sensor, audio sensor) integrated with the first and second mobile devices. In some instances, many more mobile devices are used to take data and send the data to the network for analysis.

At step 608, it is determined that each of the first and second sets of data correspond to the occurrence of an instance of an event, such that the first set of data corresponds to a first instance and the second set of data corresponds to a second instance of the event. Based at least on the occurrences of the instances of the event, an action to be performed is determined at step 610. The action may include, for instance, communicating a notification to a user of one of the mobile devices from which a set of data was received, communicating a notification to a third party regarding the instances of the event, or communicating the data itself in raw or transformed format to a third party, such as an insurance company, hospital, or governmental agency.

As mentioned, a first instance and a second instance of the event are detected by the first and second mobile devices, respectively. In one embodiment, the first and second instances are determined to have occurred simultaneously, and are both determined to be attributable to a single source. In this case, either the mobile device or the network discards to duplicate data, as only one set of data is needed for a single instance of an event, such as for a single cough. The first and second instances of the event may correspond to a cough, a sneeze, a scream, crying, a car door shutting, thunder, lightning, an explosion, an earthquake, etc. In some embodiments, the instance of the event is the event itself, such as the case of an earthquake, explosion, thunder, or lighting. But in other cases, an instance of an event, such as a cough or sneeze, correspond to an event that is different from the instance of the event. For instance, an instance of a cough or sneeze may correspond to the flu, a cold, or another health-related illness event.

In some embodiments, sets of data are received from a plurality of other mobile devices such that there are hundreds, thousands, hundreds of thousands, or millions of sets of data that the network can use to assess the occurrence of an event. Based on the received sets of data, the network may determine that a threshold number of instances of the event have occurred, at which time an action to be performed is determined. For instance, after 1000 coughs in a small region in a predetermined period of time have been detected, the network may determine that a cold virus is spreading throughout the region, and may even be able to determine that the cold virus is spreading to a neighboring region. If 1000 is the threshold number used, any number of instances of the same event (e.g., coughs) in the predetermined period of time may not be thought to be an indicator of a cold virus, but may just be attributed to random coughs.

Figure 7:
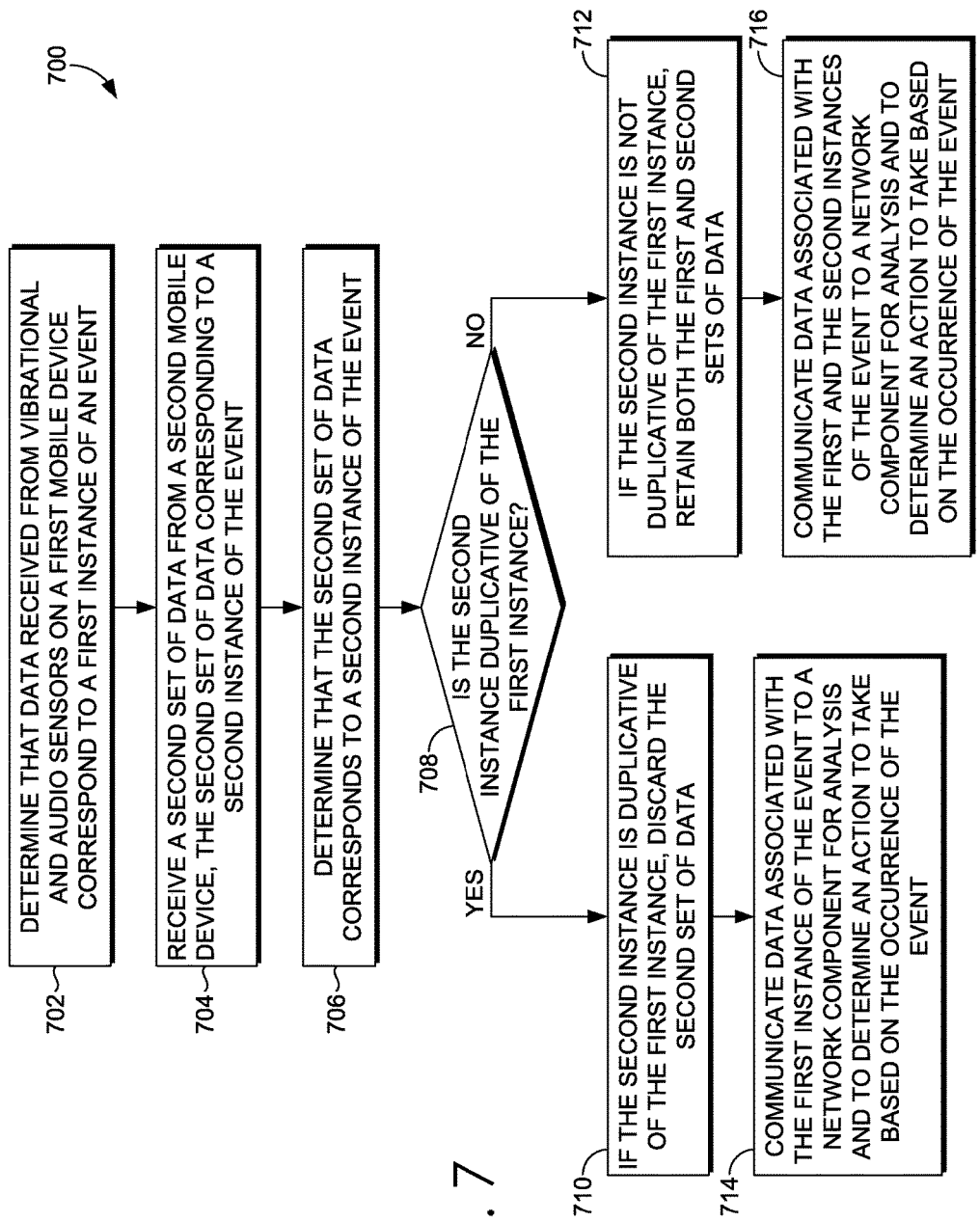

FIG. 7 illustrates a flow diagram of a method 700 for detecting an occurrence of an event based on data taken by a plurality of mobile devices, in accordance with an embodiment of the present invention. Initially at step 702, it is determined that data received by a vibrational sensor and an audio sensor on a first mobile device correspond to a first instance of an event. A second set of data from a second mobile device is received at the first mobile device, the second set of data corresponding to a second instance of the event, shown at step 704. The first and second mobile devices may form a network together to communicate data with one another. In one embodiment, even if the mobile devices utilize different communication technologies (e.g., Wi-Fi, LTE), the devices are able to communicate when a network is formed.

At step 706, it is determined that the second set of data corresponds to a second instance of the event. The first mobile device then determines, at step 708, whether the first instance is a same instance as the second instance of the event, such as the same cough, sneeze, etc., from the same individual. If the first instance is the same as the second instance, the second set of data corresponding to the second instance of the event is discarded, shown at step 710. But if the first instance is not the same as the second instance, both the first and second sets of data are retained, shown at step 712. At step 714, if data corresponding to the second instance of the event is discarded, only data associated with the first instance of the event is communicated to a network component in the wireless communications network for analysis and to determine an action to take based on the occurrences of the event. At step 716, if the two instances are different and both sets of data are retained, both the first and second sets of data are communicated to the network component in the wireless communications network. The network component may analyze the data associated with the first and/or second instance, depending on whether the data associated with the second instance has been discarded due to duplicity. If the first and second instances are not duplicative, both sets of data are communicated to the network component and are analyzed. However, if the second instance is duplicative of the first instance, the second set of data is not communicated to the network component. Further, data from a plurality of other mobile devices may also be analyzed, along with the first and second sets of data.

Figure 8:
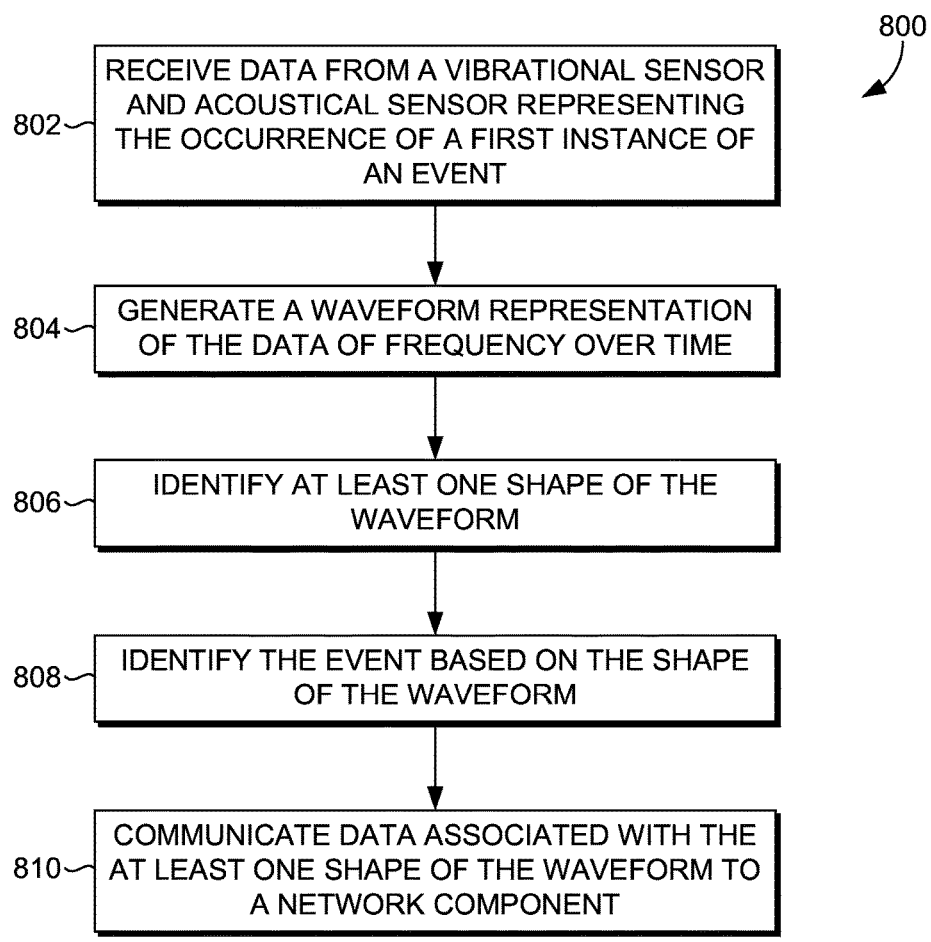

Turning now to FIG. 8, a flow diagram is depicted of a method 800 for detecting an occurrence of an event based on data taken by a plurality of mobile devices, in accordance with an embodiment of the present invention. Initially at step 802, data is received from a vibrational and an acoustical sensor, the data representing the occurrence of a first instance of an event. At step 804, a waveform representation of the data of frequency over time is generated. At least one shape that corresponds to the waveform is identified at step 806, the shape(s) containing at least a majority of the waveform within the boundaries of the shape. In embodiments, a majority is contained within the boundaries of the shape, but in other embodiments, at least 60%, at least 70%, at least 80%, or at least 90% of the waveform is encompassed within the boundaries of the shape(s). In embodiments, the percentage used by the network represents the network's desired sensitivity of the vibrational sensor and the acoustical sensor.

At step 808, the event is identified based on the shape of the waveform. As mentioned, shapes and their corresponding events may be predetermined so that when data is received, the mobile device or the network may use a lookup table or some other form of data storage and organization to determine an event that corresponds to the shape of the waveform. At step 810, data associated with the shape of the waveform is communicated to a network component. The network component may receive a plurality of data from a plurality of mobile devices, the data representing other occurrences of other instances of the event. Additionally, the network component may use the data to determine an action to be performed based on the occurrences of the first instance and the other instances of the event.

Many different arrangements of the various components depicted, as well as components not shown, are possible without departing from the scope of the claims below. Embodiments of our technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

The invention claimed is:

1. A method for detecting an occurrence of an external event based on data taken by a plurality of mobile devices, the method comprising:

determining, using the processor, that each of a first set of data and a second set of data corresponds to the occurrence of an instance of the external event based on at least one harmonic characteristic of the first and second sets of data, wherein the first set of data comprises vibration and audio data taken from a vibrational sensor and an audio sensor of a first mobile device and the second set of data comprises vibration and audio data taken from a vibrational sensor and an audio sensor of a second mobile device;

determining that the first and second sets of data occurred simultaneously, and are both attributable to a single source;

discarding the second set of data and retaining the first set of data;

communicating information determined from the first and second sets of data to a network component in the wireless communications network, the communicated data including at least location and time information; and based at least on the occurrences of the instances of the external event, determining, using the processor, an action to perform.

2. The method of claim 1, wherein the first set of data and the second set of data are received by a network component in a wireless communications network.

3. The method of claim 1, wherein each of the first mobile device and the second mobile device have an integrated vibrational sensor and an audio sensor for collecting the vibration and audio data.

4. The method of claim 1, wherein the external event corresponds to one or more of a cough, a sneeze, a scream, or a cry.

5. The method of claim 1, wherein the first set of data comprises a time stamp associated with the occurrence of the instance of the external event, frequency over time data of the occurrence of the instance of the external event, and location data.

6. The method of claim 1, further comprising anonymizing the first and the second sets of data so that the data is not traceable to a particular individual.

7. The method of claim 1, wherein the action to perform based at least on the occurrences of the instances of the external event is one or more of communicating a notification to a user of the first or the second mobile device, communicating a notification to a third party regarding the external event, or communicating the data to the third party.

8. The method of claim 1, further comprising:
receiving a plurality of sets of data from a plurality of other mobile devices;
based on the plurality of sets of data, determining that a threshold number of instances of the external event have occurred; and
determining that the action is to be performed upon the threshold number of instances of the external event having occurred.

9. Non-transitory computer-readable media having computer-executable instructions embodied thereon that, when executed, perform a method for detecting an occurrence of an external event based on data taken by a plurality of mobile devices, the method comprising:
determining that a first set of data received by a vibrational sensor and an audio sensor on the first mobile device corresponds to a first instance of an external event based on at least one harmonic characteristic of the first set of data, wherein the external event is a member of a class of events, wherein the at least one harmonic characteristic is unique and identifiable to the class of events;
receiving a second set of data from a second mobile device, the second set of data corresponding to a second instance of the external event, wherein the first and the second mobile devices communicate with one another by way of a wireless communications network;
determining that the second set of data corresponds to a second instance of the external event;
determining whether the second instance is duplicative of the first instance of the external event, such that,
  (1) if the second instance is duplicative of the first instance, discarding the second set of data that corresponds to the second instance of the external event, and
  (2) if the second instance is not duplicative of the first instance, retaining both the first set of data and the second set of data; and
communicating data associated with one or more of the first instance and the second instance of the external event to a network component in the wireless communications network, the communicated data including at least one of a time stamp associated with the occurrence of the instance of the event, frequency over time data, or location data, the network component analyzing the data associated with the one or more of the first instance and the second instance and the data received from a plurality of other mobile devices to determine an action to be performed based on the occurrence of the external event.

10. The media of claim 9, wherein the first mobile device and the second mobile device form a network to allow communication between the devices.

11. The media of claim 9, wherein if the first instance is duplicative of the second instance, the data associated with the second instance is not communicated to the network component.

12. The media of claim 11, wherein the first instance and the second instance are both determined to be one or more of a cough or a sneeze from a single individual.

13. The media of claim 9, wherein if the first instance is not duplicative of the second instance, the data associated with both the first and the second instances is communicated to the network component.

14. A method for detecting an occurrence of an event based on data taken by a plurality of mobile devices, the method comprising:
at a first mobile device, receiving data from a vibrational sensor and an acoustical sensor integrated with the first mobile device, the data representing the occurrence of a first instance of an event;
generating, using a processor, a representation of the data illustrating a waveform of frequency of one or more of sound or vibration over time;
based on the waveform, identifying, using the processor, at least one shape of the waveform, the at least one shape of the waveform being defined and determined such that at least 50% of the waveform is contained therein;
identifying, using the processor, the event based on the at least one shape of the waveform; and
communicating a portion of the data associated with the at least one shape of the waveform to a network component in the wireless communications network, the network component receiving from a plurality of mobile devices a plurality of data representing the occurrences of other instances of the event, wherein the network component analyzes the portion of the data and the plurality of data to determine an action to be performed based on the occurrences of the first instance and the other instances of the event.

15. The method of claim 14, wherein is defined and determined such that at 60% of the waveform is contained therein.

16. The method of claim 14, wherein at least the one shape is determined using a digital semaphore.

17. The method of claim 14, wherein a percentage of the waveform captured in the at least one shape is dynamic based on a desired sensitivity of the vibrational sensor and the acoustical sensor.

18. The method of claim 14, wherein the correspondence of the at least one shape of the waveform to the event is predetermined.

* * * * *